(12) United States Patent
An et al.

(10) Patent No.: US 7,611,841 B2
(45) Date of Patent: Nov. 3, 2009

(54) METHOD FOR DETECTING METHYLATION OF PROMOTER USING RESTRICTION ENZYME AND DNA CHIP

(75) Inventors: Sungwhan An, Dejeon (KR); ChiWang Yoon, Daejeon (KR); TaeJeong Oh, Daejeon (KR); DaeKyoung Yoon, Daejeon (KR); SunWoo Lee, Daejeon (KR); MyungSoon Kim, Daejeon (KR); SukKyung Woo, Daejeon (KR)

(73) Assignee: Genomictree, Inc. (KR)

( * ) Notice: Subject to any disclaimer, the term of this patent is extended or adjusted under 35 U.S.C. 154(b) by 410 days.

(21) Appl. No.: 10/983,809

(22) Filed: Nov. 8, 2004

(65) Prior Publication Data

US 2006/0063164 A1    Mar. 23, 2006

(30) Foreign Application Priority Data

Sep. 21, 2004    (KR) ............... 10-2004-0075395

(51) Int. Cl.
| | |
|---|---|
| C12Q 1/68 | (2006.01) |
| C12P 19/34 | (2006.01) |
| C12M 1/34 | (2006.01) |
| C07H 21/02 | (2006.01) |
| C07H 21/04 | (2006.01) |

(52) U.S. Cl. .................. 435/6; 435/91.1; 435/91.2; 435/287.2; 536/23.1; 536/24.3; 536/24.33

(58) Field of Classification Search ............ 435/6, 435/91-1, 91.2, 183, 283.1, 287.1, 287.2; 436/94; 536/23.1, 24.3, 24.33, 25.3, 25.32

See application file for complete search history.

(56) References Cited

U.S. PATENT DOCUMENTS

2003/0148326 A1    8/2003    Olek et al.
2005/0196792 A1*    9/2005    Fodor et al. ............... 435/6
2005/0202490 A1*    9/2005    Makarov et al. ............ 435/6

FOREIGN PATENT DOCUMENTS

| KR | 10-2004-0015705 A | 3/2004 |
|---|---|---|
| WO | WO 01/26536 | 4/2001 |

OTHER PUBLICATIONS

Adorjan, P. et al., *Nucleic Acid Res.*, 30:e21, 2002.
Ahlquist, D.A. et al., *Gastroenterol.*, 119:1219, 2000.
Chen, X.Q. et al., *Clin. Cancer Res.*, 5:2297, 1999.
Conner, B.J. et al., *PNAS*, 80:278, 1983.
Cross, S.H. et al., *Nat. Genet.*, 6:236, 1994.
Cross, S.H. & Bird A.P., *Curr. Opin. Gene Develop.*, 5:309, 1995.
De Smet, C. et al., *Mol. Cell. Bio.*, 19;7327, 1999.
Eads, C.A. et al., *Nucleic Acid Res.*, 28:e32, 2000.
Esteller, M. et al., *Cancer Res.*, 59:67, 1999.
Goessl, C. et al., *Cancer Res.*, 60:5941, 2000.
Hatada, I. et al., *PNAS*, 88:9523,1991.
Herman, J.G. et al., *PNAS*, 93:9821, 1996.
Huang, T.H. et al., *Hum. Mol. Genet.*, 8:459, 1999.
Kopreski, M.S. et al., *Clin. Cancer Res.*, 5:1961, 1999.

(Continued)

*Primary Examiner*—Frank W Lu
(74) *Attorney, Agent, or Firm*—Kelly K. Reynolds; Steven J. Hultquist; Intellectual Property / Technology Law

(57) ABSTRACT

A method for detecting the methylation of promoters using HpaII, a methylation-sensitive restriction enzyme. In such method, DNAs, derived from clinical samples or subjects to be diagnosed, are cut with HpaII, the cut DNAs are amplified by PCR with primers capable of amplifying CpG islands, and the presence or absence of the PCR amplification products is determined using a DNA chip for methylation detection. Unlike prior approaches, the inventive method allows the methylation of gene promoters to be detected in a simple and economical manner, and thus is useful for the diagnosis of diseases such as cancer that are characterized by methylation of gene promoters.

6 Claims, 6 Drawing Sheets

OTHER PUBLICATIONS

Landegren, U., Bioessays, 15:761, 1993.
Landegren, U. et al., *Science*, 241:1077, 1988.
Liang, G. et al., *Methods*, 27:150, 2002.
Malik, K. & Brown, K.W.; *Brit. J. Cancer*, 83:1583, 2000.
Miyashiro, I. et al., *Clin. Chem.*, 47:505, 2001.
Palmisano, W.A. et al., *Cancer Res.*, 60:5954, 2000.
Robertson, K.D. & Jones, P.A., *Carcinogensis*, 21:461, 2000.
Saiki, R.K. et al., *Nature*, 324:163, 1986.
Sanchez-Cespedes, M. et al., *Cancer Res.*, 60:892, 2000.
Sato, N. et al., *Cancer Research*, 63:3735, 2003.
Shi, H. et al., *J. Cell Biochem.*, 88:138, 2003.
Singal, R. & Ginder, G.D., *Blood*, 93:4059, 1999.
Sozzi, G. et al., *Clin. Cancer Res.*, 5:2689, 1999.
Sueoka, E. et al., *Cancer Res.*, 59:1404, 1999.
Tsou, J.A. et al., *Oncogene*, 21:5450, 2002.
Virmani, A.K. et al., *J. Natl. Cancer Institut.*, 92:1303, 2000.
Xiong, Z. & Laird, P.W., *Nucleic Acid Res.*, 25:2532, 1997.
Yan, P.S. et al., *Clin. Cancer Res.*, 6:1432, 2000.

* cited by examiner

SEQUENCE LISTING

<160> NUMBER OF SEQ ID NOS: 48

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
tcaacggatt tggtcgtatt                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
tagaggcagg gatgatgttc                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
cccagatcat gtttgagacc                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
gcagtgatct ccttctgcat                                               20

<210> SEQ ID NO 5
<211> LENGTH: 23
<212> TYPE: DNA
<213> ORGANISM: Artificial Sequence
<220> FEATURE:
<223> OTHER INFORMATION: Synthetic Construct

<400> SEQUENCE: 5
gggtgtgaac catgagaagt atg                                           23

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
ggcagggatg atgttctgga g                                             21

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct

<400> SEQUENCE: 7
ggctgtgcta tccctgtacg c                                              21

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
ccagggcgac gtagcacagc                                                20

<210> SEQ ID NO 9
<211> LENGTH: 23
<212> TYPE: DNA
<213> ORGANISM: Artificial Sequence
<220> FEATURE:
<223> OTHER INFORMATION: Synthetic Construct

<400> SEQUENCE: 9
gcagagagag agtcttggct ttc                                            23

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct

<400> SEQUENCE: 10
cttgactgcc gaccagtcct g                                              21

<210> SEQ ID NO 11
<211> LENGTH: 23
<212> TYPE: DNA
<213> ORGANISM: Artificial Sequence
<220> FEATURE:
<223> OTHER INFORMATION: Synthetic Construct

<400> SEQUENCE: 11
gtgacagaag tagtaggaag tga                                            23

<210> SEQ ID NO 12
<211> LENGTH: 22
<212> TYPE: DNA
<213> ORGANISM: Artificial Sequence
<220> FEATURE:
<223> OTHER INFORMATION: Synthetic Construct

<400> SEQUENCE: 12
gatctcccTt gcactgaatg tc                                             22

<210> SEQ ID NO 13
<211> LENGTH: 22
<212> TYPE: DNA
<213> ORGANISM: Artificial Sequence
<220> FEATURE:
<223> OTHER INFORMATION: Synthetic Construct

```
<400> SEQUENCE: 13
gggggtattg tttggaggtt gg                                          22

<210> SEQ ID NO 14
<211> LENGTH: 26
<212> TYPE: DNA
<213> ORGANISM: Artificial Sequence
<220> FEATURE:
<223> OTHER INFORMATION: Synthetic Construct

<400> SEQUENCE: 14
aaaaattcac ccctaactaa ccaaac                                      26

<210> SEQ ID NO 15
<211> LENGTH: 24
<212> TYPE: DNA
<213> ORGANISM: Artificial Sequence
<220> FEATURE:
<223> OTHER INFORMATION: Synthetic Construct

<400> SEQUENCE: 15
ggtaggaggg tttatttttt gtta                                        24

<210> SEQ ID NO 16
<211> LENGTH: 23
<212> TYPE: DNA
<213> ORGANISM: Artificial Sequence
<220> FEATURE:
<223> OTHER INFORMATION: Synthetic Construct

<400> SEQUENCE: 16
cccaaaaaaa tcccaaattc tcc                                         23

<210> SEQ ID NO 17
<211> LENGTH: 22
<212> TYPE: DNA
<213> ORGANISM: Artificial Sequence
<220> FEATURE:
<223> OTHER INFORMATION: Synthetic Construct

<400> SEQUENCE: 17
caggcaaccc agacgtccag ag                                          22

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
cagtgccacc ctggcgggct                                             20

<210> SEQ ID NO 19
<211> LENGTH: 22
<212> TYPE: DNA
<213> ORGANISM: Artificial Sequence
<220> FEATURE:
<223> OTHER INFORMATION: Synthetic Construct

<400> SEQUENCE: 19
ccgtgcaatt ccattctctg ga                                          22
```

```
<210> SEQ ID NO 20
<211> LENGTH: 21
<212> TYPE: DNA
<213> ORGANISM: Artificial Sequence
<220> FEATURE:
<223> OTHER INFORMATION: Synthetic Construct

<400> SEQUENCE: 20
cgcacagaac gagcggagtt c                                              21

<210> SEQ ID NO 21
<211> LENGTH: 19
<212> TYPE: DNA
<213> ORGANISM: Artificial Sequence
<220> FEATURE:
<223> OTHER INFORMATION: Synthetic Construct

<400> SEQUENCE: 21
gctgcctgcc ccctgatgc                                                 19

<210> SEQ ID NO 22
<211> LENGTH: 19
<212> TYPE: DNA
<213> ORGANISM: Artificial Sequence
<220> FEATURE:
<223> OTHER INFORMATION: Synthetic Construct

<400> SEQUENCE: 22
ccccaggcac caccactcc                                                 19

<210> SEQ ID NO 23
<211> LENGTH: 22
<212> TYPE: DNA
<213> ORGANISM: Artificial Sequence
<220> FEATURE:
<223> OTHER INFORMATION: Synthetic Construct

<400> SEQUENCE: 23
ggatcagagt tggaagagtc cc                                             22

<210> SEQ ID NO 24
<211> LENGTH: 19
<212> TYPE: DNA
<213> ORGANISM: Artificial Sequence
<220> FEATURE:
<223> OTHER INFORMATION: Synthetic Construct

<400> SEQUENCE: 24
cctcccagcg ccagcgact                                                 19

<210> SEQ ID NO 25
<211> LENGTH: 20
<212> TYPE: DNA
<213> ORGANISM: Artificial Sequence
<220> FEATURE:
<223> OTHER INFORMATION: Synthetic Construct

<400> SEQUENCE: 25
ggacccgact cgcaaactgt                                                20

<210> SEQ ID NO 26
<211> LENGTH: 19
<212> TYPE: DNA
<213> ORGANISM: Artificial Sequence
<220> FEATURE:
<223> OTHER INFORMATION: Synthetic Construct
```

```
<400> SEQUENCE: 26
gctggcgtgg tgcgtccct                                                19

<210> SEQ ID NO 27
<211> LENGTH: 21
<212> TYPE: DNA
<213> ORGANISM: Artificial Sequence
<220> FEATURE:
<223> OTHER INFORMATION: Synthetic Construct

<400> SEQUENCE: 27
ccacagttct ctcattccag c                                             21

<210> SEQ ID NO 28
<211> LENGTH: 23
<212> TYPE: DNA
<213> ORGANISM: Artificial Sequence
<220> FEATURE:
<223> OTHER INFORMATION: Synthetic Construct

<400> SEQUENCE: 28
ctcaggattc tttttgcagc aac                                           23

<210> SEQ ID NO 29
<211> LENGTH: 23
<212> TYPE: DNA
<213> ORGANISM: Artificial Sequence
<220> FEATURE:
<223> OTHER INFORMATION: Synthetic Construct

<400> SEQUENCE: 29
gctacccaag aggacgaaat aaa                                           23

<210> SEQ ID NO 30
<211> LENGTH: 20
<212> TYPE: DNA
<213> ORGANISM: Artificial Sequence
<220> FEATURE:
<223> OTHER INFORMATION: Synthetic Construct

<400> SEQUENCE: 30
ctggctgcac tacggtcagg                                               20

<210> SEQ ID NO 31
<211> LENGTH: 22
<212> TYPE: DNA
<213> ORGANISM: Artificial Sequence
<220> FEATURE:
<223> OTHER INFORMATION: Synthetic Construct

<400> SEQUENCE: 31
ggtacacagg ccatatagga ac                                            22

<210> SEQ ID NO 32
<211> LENGTH: 20
<212> TYPE: DNA
<213> ORGANISM: Artificial Sequence
<220> FEATURE:
<223> OTHER INFORMATION: Synthetic Construct

<400> SEQUENCE: 32
ccgaatccct gggcatcagg                                               20
```

```
<210> SEQ ID NO 33
<211> LENGTH: 20
<212> TYPE: DNA
<213> ORGANISM: Artificial Sequence
<220> FEATURE:
<223> OTHER INFORMATION: Synthetic Construct

<400> SEQUENCE: 33
cctccagcgt tgccaactgg                                                     20

<210> SEQ ID NO 34
<211> LENGTH: 20
<212> TYPE: DNA
<213> ORGANISM: Artificial Sequence
<220> FEATURE:
<223> OTHER INFORMATION: Synthetic Construct

<400> SEQUENCE: 34
cgtctgggct caagctccta                                                     20

<210> SEQ ID NO 35
<211> LENGTH: 20
<212> TYPE: DNA
<213> ORGANISM: Artificial Sequence
<220> FEATURE:
<223> OTHER INFORMATION: Synthetic Construct

<400> SEQUENCE: 35
gtgagcgcca tcgtgcttgc                                                     20

<210> SEQ ID NO 36
<211> LENGTH: 20
<212> TYPE: DNA
<213> ORGANISM: Artificial Sequence
<220> FEATURE:
<223> OTHER INFORMATION: Synthetic Construct

<400> SEQUENCE: 36
caccactttc agctgagggg                                                     20

<210> SEQ ID NO 37
<211> LENGTH: 501
<212> TYPE: DNA
<213> ORGANISM: Homo sapiens

<400> SEQUENCE: 37
gcagagagag agtcttggct ttcacgggaa tcaaggtgag gactctgagg gcggatgaga         60
agacctctcc ccaaaaaagg cacattcaca gagccctgcc gctgctgtca ggcctgtgag        120
gccaggcagg ggtggcctgt ttggcacgct tagatttcca cagtgggggc tgagggaggt        180
gggggtattg tttggaggct ggcggatttg ggtcagcacg catattcgtc ccaggctgct        240
agatactgag gtgaggaccc tagtggagac gaagggacca gcaacgctag aacagtgacg        300
tccggtagcg tccagccgtc agcccctcag acgccacggg ctgccggatg tgagtcatcc        360
tgacttccgc tttgaaaaaa aagacccgag cggatgtggc tcatcctgac ttccgctttg        420
gaggcgagga cccagcgag tgtaggggg gcggcgtctg gtcagccagg ggtgaattct        480
caggactggt cggcagtcaa g                                                  501

<210> SEQ ID NO 38
<211> LENGTH: 575
<212> TYPE: DNA
<213> ORGANISM: Homo sapiens
```

```
<400> SEQUENCE: 38
caggcaaccc agacttccag agttctgatc tccactacta agctgctagc atagctttc      60 tggtaactat ttttaattca aatataattc gagtgatcta tctaacaagt catcactctg    120
acaactcagt gacttgtaat gtaaaattat tcattgtaat tcatttaata ttattgtttc    180
tctgtgctgc aaaaatcata gcaatcgaga tgtaatttat tactctccct cccacctccg    240
gcatcttgtg ctaatccttc tgccctgcgg acctcccccg actctttact atgcgtgtca    300
actgccatca acttccttgc ttgctgggga ctggggccgc gagggcatac ccccgagggg    360
tacggggcta gggctaggca ggctgtgcgg ttgggcgggg ccctgtgccc cactgcggag    420
tgcgggtcgg aagcggaga gagaagcagc tgtgtaatcc gctggatgcg gaccagggcg     480
ctccccattc ccgtcgggag cccgccgatt ggctgggtgt gggcgcacgt gaccgacatg    540
tggctgtatt ggtgcagccc gccagggtgt cactg                               575

<210> SEQ ID NO 39
<211> LENGTH: 402
<212> TYPE: DNA
<213> ORGANISM: Homo sapiens

<400> SEQUENCE: 39
ccgtgcaatt ccattctctg gaaaagtgga atcagctggc attgcccagc gtgatttgtg    60
aggctgagcc ccaacagtcc aaagaagcaa atgggatgcc acctccgcgg ggctcgctcc   120
tcgcgaggtg ctcaccccgt atctgccatg caaaacgagg gagcgttagg aaggaatccg   180
tcttgtaaag ccattggtcc tggtcatcag cctctaccca atgctttcgt gatgctgctg   240
ctgatctatt tgggaagttg gctggctggc gaggcagagc ctctcctcaa agcctggctc   300
ccacggaaaa tatgctcagt gcagccgcgt gcatgaatga aaacgccgcc gggcgcttct   360
agtcggacaa aatgcagccg agaactccgc tcgttctgtg cg                      402

<210> SEQ ID NO 40
<211> LENGTH: 339
<212> TYPE: DNA
<213> ORGANISM: Homo sapiens

<400> SEQUENCE: 40
gctgcctgcc ccctgatgct ccctgcccca ccctgtgcag taggaaccca gccatggtga    60
acgaagccag aggaaacagc agcctcaacc cctgcttgga gggcagtgcc agcagtggca   120
gtgagagctc caaagatagt tcgagatgtt ccaccccggg cctggaccct gagcggcatg   180
agagactccg ggagaagatg aggcggcgat tggaatctgg tgacaagtgg ttctccctgg    240
aattcttccc tcctcgaact gctgagggag ctgtcaatct catctcaagg taaactcatg    300
caaggttaag gtgggaggcg ggagtggtgg tgcctgggg                          339

<210> SEQ ID NO 41
<211> LENGTH: 374
<212> TYPE: DNA
<213> ORGANISM: Homo sapiens

<400> SEQUENCE: 41
ggatcagagt tggaagagtc cctacaatcc tggacccttt ccgccaaatc gtgaaaccag     60
gggtggagtg gggcgagggt tcaaaaccag gccggactga gaggtgaaat tcaccatgac    120
gtcaaactgc cctcaaattc ccgctcactt taagggcgtt acttgttggt gcccccacca    180
tcccccacca tttccatcaa tgacctcaat gcaaatacaa gtgggacggt cctgctggat    240
```

-continued

```
cctccaggtt ctggaagcat gagggtgacg caacccaggg gcaaaggacc cctccgccca    300
ttggttgctg tgcactggcg gaactttccc gacccacagc ggcgggaata agagcagtcg    360
ctggcgctgg gagg                                                      374

<210> SEQ ID NO 42
<211> LENGTH: 192
<212> TYPE: DNA
<213> ORGANISM: Homo sapiens

<400> SEQUENCE: 42
ggacccgact cgcaaactgt tgcatttgct ctccacctcc cagcgccccc tccgagatcc     60
cggggagcca gcttgctggg agagcgggac ggtccggagc aagcccagag gcagaggagg    120
cgacagaggg aaaaagggcc gagctagccg ctccagtgct gtacaggagc cgaagggacg    180
caccacgcca gc                                                        192

<210> SEQ ID NO 43
<211> LENGTH: 571
<212> TYPE: DNA
<213> ORGANISM: Homo sapiens

<400> SEQUENCE: 43
ccacagttct ctcattccag cttccctggt gggatcaacc tgggcctctc tgggccttcc     60
cccttggaag aactctctgt gaagtgctga agtgttgact gaagggtttt tttttttttt    120
tttttttttt gagatggagt ctcgctctgt cgcccaggct ggagtacagt ggtgtgatct    180
cagctcactg caaactcccc ctcccaggtt cacgccattt ccctgcctca gcctcccgag    240
tagctgggac tgcaggcgcc caccaccatg cccggctaat ttttttgtat tttagtagag    300
gatgggtttt caccatgtta gccaggatgg tctcgatctc ctgatctcgt gatccaccca    360
tctcggcctc ccaaagtgct gggattacag gagtaagcca ccgcgcccgg ccgactgaag    420 ggttttctc caggttcctc tgtgaggtct cagtgcaggg gttgctctga ggccctcccc    480
tggatatctc agtctagggg cccttctttg ggggtctagg cctaggagca ggaggtgtgc    540
atgtgggcgt tgctgcaaaa agaatcctga g                                  571

<210> SEQ ID NO 44
<211> LENGTH: 630
<212> TYPE: DNA
<213> ORGANISM: Homo sapiens

<400> SEQUENCE: 44
gctacccaag aggacgaaat aaagaagcag gaaacgaagc ctgcggctaa accctggaga     60
tgactattag gaaaacacca gaggatgccc cgcccgccag cccacaatga gcagcctgtc    120
caagtcacaa agcggggcct cgggccttga cagttcgcga tctgtaagca gaatgttcca    180
gggcctccct gtcgcctgca tccagcctgg gggccatctt cactggtgtg ggaggccgaa    240
agtggacggc gacggaggcc cctctggtta tctctttgcc gtgccaacac agtctctgcg    300
cccactaaga tgcatgaaat aaaaatttcc gtgactcgcc ctttgcagtg agacctgaa    360 acaggcacac cagggaattg gagcggagga gggtaactca aactcagagt gagagggttt    420 gcaggggcc gatttgggc caacaggctt cccagcaggc cccgcgcg gacagcgga    480 aggcgaaacg ctttcaagag accccgctgc caacatcccc acgccctcgc gccctcccgc    540
cgccccagaa ggccaactcc gcctgcctga gtcacagctg gagctgggga ggagccaggg    600
aaaggaggcc cctgaccgta gtgcagccag                                    630
```

<210> SEQ ID NO 45
<211> LENGTH: 469
<212> TYPE: DNA
<213> ORGANISM: Homo sapiens

<400> SEQUENCE: 45

| | | | | | | |
|---|---|---|---|---|---|---|
| gtgacagaag | tagtaggaag | tgagctgttc | agaggcagga | gggtctattc | tttgccaaag | 60 |
| ggggaccag | aattccccca | tgcgagctgt | tgaggactg | ggatgccgag | aacgcgagcg | 120 |
| atccgagcag | ggtttgtctg | gcaccgtcg | gggtaggatc | cggaacgcat | tcggaaggct | 180 |
| ttttgcaagc | atttacttgg | aaggagaact | tgggatcttt | ctgggaaccc | cccgccccgg | 240 |
| ctggattggc | cgagcaagcc | tggaaaatgg | taaatgatca | tttggatcaa | ttacaggctt | 300 |
| ttagctggct | tgtctgtcat | aattcatgat | tcggggctgg | gaaaaagacc | aacagcctac | 360 |
| gtgccaaaaa | aggggcagag | tttgatggag | ttgggtggac | ttttctatgc | catttgcctc | 420 |
| cacacctaga | ggataagcac | ttttgcagac | attcagtgca | agggagatc | | 469 |

<210> SEQ ID NO 46
<211> LENGTH: 620
<212> TYPE: DNA
<213> ORGANISM: Homo sapiens

<400> SEQUENCE: 46

| | | | | | | |
|---|---|---|---|---|---|---|
| ggtacacagg | ccatatagga | acttaaatct | tatttaaaca | ctattttaat | agtgtgttaa | 60 |
| cgtgtaaaat | atttaagcat | tccagcttga | agccaaggaa | ttgtatccag | tcgttcaagc | 120 |
| aatgtatgtt | cagtaaaatc | acctgcagag | caaaagtctg | ttgactaact | accgcctccc | 180 |
| ccgcccccc | accacccccc | gcaggcggtt | tctgggtgaa | gcagatgttt | tcttaaaat | 240 |
| ttgtcatcat | tgactttagg | tttcttttgg | caggttttg | gcacccaaaa | cagtgtgagc | 300 |
| tctctttca | gctttattca | cctgtgctgg | gaggggagct | aggataattc | ttggctgccg | 360 |
| aaggatttag | gcagtgcgtg | tgcatctgcc | cgggtccccc | ccgttttag | ggtcagtgca | 420 |
| cttttttgt | cttttcgtga | ccctgactaa | agagaaagga | tgtcaaggga | atgaaaatcc | 480 |
| tggaatgtgt | ctgatcattt | gaaatgtaca | aaattgggca | gataagctgc | atggctaaat | 540 |
| tgttaggagg | aagaggcaag | gcagtagtgg | agaaggggga | ggcagtggat | cccacacaag | 600 |
| cctgatgccc | agggattcgg | | | | | 620 |

<210> SEQ ID NO 47
<211> LENGTH: 444
<212> TYPE: DNA
<213> ORGANISM: Homo sapiens

<400> SEQUENCE: 47

| | | | | | | |
|---|---|---|---|---|---|---|
| cctccagcgt | tgccaactgg | acctaaagag | aggccgcgac | tgtcgcccac | ctgcgggatg | 60 |
| ggcctggtgc | tgggcggtca | ggacactgac | ctggaaggag | cgcgcgcgag | ggagggaggc | 120 |
| tgggagtcag | aatcggaaa | gggaggtgcg | gggcggcgag | ggagcgaagg | aggagaggag | 180 |
| gaaggagcgg | gaggggtgct | ggcggggtg | cgtagtgggt | ggagaaagcc | gctagagcaa | 240 |
| atttggggcc | ggaccaggca | gcactcggct | tttaacctgg | gcagtgaagg | cggggaaag | 300 |
| agcaaaagga | aggggtggtg | tgcggagtag | gggtgggtgg | ggggaattgg | aagcaaatga | 360 |
| catcacagca | ggtcagagaa | aaagggttga | gcggcaggca | cccagagtag | taggtctttg | 420 |
| gcattaggag | cttgagccca | gacg | | | | 444 |

```
<210> SEQ ID NO 48
<211> LENGTH: 333
<212> TYPE: DNA
<213> ORGANISM: Homo sapiens

<400> SEQUENCE: 48
gtgagcgcca tcgtgcttgc cttcggcttg ctctgggccc cctaccacgc agtcaacctt      60
ctgcaggcgg tcgcagcgct ggctccaccg gaagggcct tggcgaagct gggcggagcc     120
ggccaggcgg cgcgagcggg aactacggcc ttggccttct tcagttctag cgtcaacccg    180
gtgctctacg tcttcaccgc tggagatctg ctgccccggg caggtccccg tttcctcacg    240
cggctcttcg aaggctctgg ggaggcccga ggggcggcc gctctaggga agggaccatg      300
gagctccgaa ctaccctca gctgaaagtg gtg                                   333
```

METHOD FOR DETECTING METHYLATION OF PROMOTER USING RESTRICTION ENZYME AND DNA CHIP

CROSS-REFERENCE TO RELATED APPLICATION

This application claims priority under 35 USC 119 of Korean Patent Application No. 10-2004-0075395 filed Sep. 21, 2004.

BACKGROUND OF THE INVENTION

1. Field of the Invention

The present invention relates to a method for detecting the methylation of promoters using HpaII, which is a methylation-sensitive restriction enzyme, and more particularly to a method for detecting the methylation of promoters, which comprises cutting DNA derived from clinical samples or subjects to be diagnosed with restriction enzyme HpaII, amplifying the cut DNA by polymerase chain reaction (PCR) with primers capable of amplifying CpG islands, and determining the presence or absence of the PCR amplification products with a DNA chip for methylation detection.

2. Background of the Related Art

In current clinical practice, the diagnosis of cancer is confirmed by finally performing tissue biopsy after history taking, physical examination and clinical assessment, followed by radiographic testing and endoscopy if cancer is suspected. However, the diagnosis of cancer by the existing clinical practices is possible only when the number of cancer cells is more than a billion, and the diameter of cancer is more than 1 cm. Meanwhile a tumor marker for detecting a substance, which is directly or indirectly produced by cancer in blood is used in cancer screening tests, but it has limitations in accuracy so that it often shows false positive or false negative.

Thus, in order to diagnose and treat cancer at the root, approaches at a gene level need to be performed. Recently, genetic analysis has been actively attempted to diagnose cancer. The simplest typical method is to detect the presence of ABL:BCR fusion genes (genetic characteristic of leukemia) in blood by PCR. Such method has an accuracy of more than 95%, and after the diagnosis and therapy of chronic myelocytic leukemia, this method is being used for the assessment of the result and follow-up study, etc. However, this method has the shortcoming that it can be applied only to some blood cancers.

Furthermore, another method is being attempted, in which the presence of genes expressed by cancer cells is detected by RT-PCR and blotting, thereby diagnosing cancer cells present in blood cells. However, this method has shortcomings in that it can be applied only to some cancers, including prostate cancer and melanoma, and has a high false positive rate. Also, it is difficult to standardize detection and reading in this method, and its utility is also limited (Kopreski, M. S. et al., Clin. Cancer Res., 5:1961, 1999; Miyashiro, I. et al., Clin. Chem., 47:505, 2001).

Recently, genetic testing using a DNA in serum or plasma has been actively attempted. This is a method of detecting a cancer-related gene that is isolated from cancer cells and released into blood and is present in the form of a free DNA in serum. It is found that the concentration of DNA in serum is 5-10 times increased in actual cancer patients as compared to that of normal persons, and such increased DNA is released mostly from cancer cells. The analysis of cancer-specific gene abnormalities, such as the mutation, deletion and functional loss of oncogenes and tumor-suppressor genes, using such DNAs isolated from cancer cells, allows the diagnosis of cancer. There has been an active attempt to diagnose lung cancer, head and neck cancer, breast cancer, colon cancer, and liver cancer, etc., by examining the promoter methylation of mutated K-Ras oncogenes, p53 tumor-suppressor genes and p16 genes in serum, and the labeling and instability of microsatellite (Chen, X. Q. et al., Clin. Cancer Res., 5:2297, 1999; Esteller, M. et al., Cancer Res., 59:67, 1999; Sanchez-Cespedes, M. et al., Cancer Res., 60:892, 2000; Sozzi, G. et al., Clin. Cancer Res., 5:2689, 1999).

Meanwhile, in samples other than blood, the DNA of cancer cells can also be detected. A method is being attempted in which the presence of cancer cells or oncogenes in sputum or bronchoalveolar lavage of lung cancer patients is detected by a gene or antibody test (Palmisano, W. A. et al., Cancer Res., 60:5954, 2000; Sueoka, E. et al., Cancer Res., 59:1404, 1999). Also, other methods of detecting the presence of oncogenes in feces of colon and rectal cancer patients (Ahlquist, D. A. et al., Gastroenterol., 119:1219, 2000) and detecting promoter methylation abnormalities in urine and prostate fluid (Goessl, C. et al., Cancer Res., 60:5941, 2000) are being attempted. However, in order to accurately diagnose cancers that cause a large number of gene abnormalities and show various mutations according to each cancer, a method, by which a large number of genes are simultaneously analyzed in an accurate and automatic manner, is required. However, such a method is not yet established.

Accordingly, methods of diagnosing cancer by the measurement of DNA methylation are being proposed. When the promoter CpG island of a certain gene is over-methylated, the expression of such a gene is silenced. This is interpreted to be a main mechanism in which the function of this gene is lost even when there is no mutation in the protein-coding sequence of the gene in a living body. Also, this is analyzed as a factor by which the function of a number of tumor-suppressor genes in human cancer is lost. Thus, detection of the methylation of the promoter CpG island of tumor-suppressor genes is greatly needed for the study of cancer, and recently, an attempt is actively being conducted in which the promoter methylation by a method, such as methylation-specific PCR (hereinafter, referred to as MSP) or automatic DNA sequencing is examined, thereby enabling the diagnosis and screening of cancer.

For the accurate diagnosis of cancer, it is important to detect not only a mutated gene but also a mechanism by which the mutation of this gene occurs. While previous studies have been conducted by focusing on the mutations of a coding sequence, i.e., micro-changes, such as point mutations, deletions and insertions, or macroscopic chromosomal abnormalities, recently, epigenetic changes are reported to be as important as these mutations, and a typical example of the epigenetic changes is the methylation of promoter CpG islands.

In the genomic DNA of mammal cells, there is the fifth base in addition to A, C, G and T, which is 5-methylcytosine where a methyl group is attached to the fifth carbon of the cytosine ring (5-mC). 5-mC is always attached only to the C of a CG dinucleotide (5'-mCG-3'), which is generally marked CpG. The methylation of this CpG inhibits a repetitive DNA sequence in genomes, such as alu or transposon, from being expressed. Also, this CpG is a site where an epigenetic change in mammal cells occurs most often. The 5-mC of this CpG is naturally deaminated to T, and thus, the CpG in mammal genomes shows only 1% of frequency, which is much lower than a normal frequency ($¼ × ¼ = 6.25\%$).

Regions in which CpG is exceptionally integrated are known as CpG islands. The CpG islands refer to sites that are 0.2-3 kb in length, and have a C+G content of more than 50% and a CpG ratio of more than 3.75%. There are about 45,000 CpG islands in the human genome, and they are mostly found in promoter regions regulating the expression of genes. Actually, the CpG islands occur in the promoters of housekeeping genes accounting for about 50% of human genes (Cross, S. H. & Bird, A. P., *Curr. Opin. Gene Develop.*, 5:309, 1995).

Meanwhile, in the somatic cells of normal persons, the CpG islands of such housekeeping gene promoter sites are un-methylated, but imprinted genes and the genes on inactivated X chromosomes are methylated such that they are not expressed during development.

During a cancer-causing process, methylation is found in promoter CpG islands, and the restriction on the corresponding gene expression occurs. Particularly, if methylation occurs in the promoter CpG islands of tumor-suppressor genes that regulate cell cycle or apoptosis, restore DNA, participate in the adhesion of cells and the interaction between cells, and suppress cell invasion and metastasis, it blocks the expression and function of such genes in the same manner as the mutations of a coding sequence, thereby promoting the development and progression of cancer. In addition, partial methylation also occurs in the CpG islands according to aging.

An interesting fact is that, in the case of genes whose mutations are attributed to the development of cancer in congenital cancer but does not occur in acquired cancer, the methylation of promoter CpG islands occurs instead of mutation. Typical examples include the promoter methylation of genes, such as acquired renal cancer VHL (von Hippel Lindau), breast cancer BRCA1, colon cancer MLH1, and stomach cancer E-CAD. In addition, in about half of all cancers, the promoter methylation of p16 or the mutation of Rb occurs, and the remaining cancers show the mutation of p53 or the promoter methylation of p73, p14 and the like.

An important fact is that an epigenetic change caused by this promoter methylation causes a genetic change (i.e., the mutation of a coding sequence), and the development of cancer is progressed by the combination of such genetic and epigenetic changes.

Most of cancers show three common characteristics with respect to CpG, namely, hypermethylation of the promoter CpG islands of tumor-suppressor genes, the hypomethylation of the remaining CpG base sites, and an increase in the activity of methylation enzyme, i.e., DNA cytosine methyltransferase (DNMT) (Singal, R. & Ginder, G. D., *Blood*, 93:4059, 1999; Robertson, K. & Jones, P. A., *Carcinogensis*, 21:461, 2000; Malik, K. & Brown, K. W., *Brit. J. Cancer*, 83:1583, 2000).

When promoter CpG islands are methylated, the reason why the expression of the corresponding genes is blocked is not clearly established, but presumed to be because a methyl CpG-binding protein (MECP) or a methyl CpG-binding domain protein (MBD), and histone deacetylase, bind to methylated cytosine thereby causing a change in the chromatin structure of chromosomes and a change in histone protein.

There is a dispute about whether the methylation of promoter CpG islands directly causes the development of cancer or is a secondary change after the development of cancer. However, it is clear that the promoter methylation of tumor-related genes is an important index to cancer, and thus, can be used in many applications, including the diagnosis and early detection of cancer, the prediction of the risk of the development of cancer, the prognosis of cancer, follow-up examination after treatment, and the prediction of a response to anti-cancer therapy. Recently, an actual attempt to examine the promoter methylation of tumor-related genes in blood, sputum, saliva, feces or urine and to use the examined results for the diagnosis and treatment of various cancers, is being actively conducted (Esteller, M. et al., *Cancer Res.*, 59:67, 1999; Sanchez-Cespedez, M. et al., *Cancer Res.*, 60:892, 2000; Ahlquist, D. A. et al., *Gastroenterol.*, 119:1219, 2000).

In order to maximize the accuracy of cancer diagnosis using promoter methylation, analyze the development of cancer according to each stage and discriminate a change according to cancer and aging, an examination that can accurately analyze the methylation of all the cytosine bases of promoter CpG islands is required. Currently, a standard method for this examination is a bisulfite genome-sequencing method, in which a sample DNA is treated with sodium bisulfite, and all regions of the CpG islands of a target gene to be examined are amplified by PCR, and then, the base sequence of the amplified regions is analyzed. However, this examination has a problem in that there are limitations on the number of genes or samples that can be examined at a time. Other problems are that automation is difficult, and much time and expense are required.

In Johns Hopkins University, MD Anderson Cancer Center and Medical University of Berlin, etc., studies on the promoter methylation of cancer-related genes are being actively conducted. The fundamental data thus obtained are interchanged through the DNA Methylation Society (DMS) and stored in MethDB, a publicly available DNA methylation database established in 2000 (world wide web address www-.methdb.de). Meanwhile, EpiGenX Pharmaceuticals, Inc. is now developing therapeutic agents associated with the methylation of CpG islands, and Epigenomics, Inc. is now conducting studies to apply promoter methylation to cancer diagnosis by examining the promoter methylation using various techniques, such as DNA chips and MALDI-TOF.

Until now, many methods have been attempted to measure the methylation pattern of certain gene promoters. First methods, which comprises cutting each CpG site with a methylation-specific enzyme and then subjecting the cut sites to Southern blot analysis or artificial PCR, have been used (Hatada, I. et al., *PNAS*, 88:9523, 1991; Liang, G. et al., *Methods*, 27:150, 2002). Other methods that have been used in the art include methylation-specific PCR (MSP) (Herman, J. G. et al., *PNAS*, 93:9821, 1996), MethylLight assay (Eads, C. A. et al., *Nucleic Acid Res.*, 28:e42, 2000), and COBRA (Xiong, Z. & Laird, P. W., *Nucleic Acid Res.*, 25:2532, 1997) using DNA modification with sodium bisulfite. However, such technologies are disadvantageous in that they are expensive or difficult to use in clinical applications.

With the recent development of high-throughput analysis technology, assays allowing CpG island methylation to be analyzed at a genome level were developed. Oligonucleotide-based methylation assays using PCR after bisulfite treatment were developed by Adorjan, et al. (Adorjan, P. et al., *Nucleic Acid Res.*, 30:e21, 2002) and Shi et al. (Shi, H. et al., *J. Cell Biochem.*, 88:138, 2003), and also methods such as DMH (Huang, H. T. et al., *Human Mol. Genet.*, 8:459, 1999), CGI (Yan, P. S. et al., *Clin. Cancer Res.*, 6:1432, 2000) and ECISTs (Tsou, J. A. et al., *Oncogene*, 21:5450, 2002) were developed. Methylation assays using DNA chip include a method comprising modifying the cytosine of genomic DNA into uracil, amplifying the modified DNA, polymerizing the amplification product into oligonucleotide or PNA-oligomer, and hybridizing the polymer in a DNA chip (Korean Patent Laid-open Publication No. 10-2004-0015705).

Such methods have improvements in efficiency and high-throughput analysis over the prior methods, but have problems in that a long time is required and the preparation of samples is complex, thus making it difficult to use such methods in clinical applications. Accordingly, there is now a need for the development of new methodology that can detect methylation quickly in a simple and inexpensive manner and in ever increasing quantities.

SUMMARY OF THE INVENTION

Therefore, the present inventors have conducted extensive studies to develop a method of detecting the methylation of disease-associated gene promoters in a simple and economical manner. During our studies, sample DNA was treated with HpaII, which is a methylation-sensitive restriction enzyme having the characteristics that it recognizes and cuts a 5'-CCGG-3' base sequence present in a CpG island, and at the same time, does not cut the base sequence when the second cytosine of the base sequence has been methylated. Then, the treated DNA was amplified by PCR with primers capable of amplifying the CpG island of a promoter, and the presence or absence of the PCR amplification products was determined with a DNA chip for methylation detection. As a result, the present inventors have found that such a method allows the methylation of the promoter to be detected in a rapid and accurate manner at a low cost, thereby perfecting the present invention.

The method of the present invention enables detection of the methylation of gene promoters derived from clinical samples or subjects to be diagnosed, in a rapid, accurate and cost-effective manner.

In one aspect, the present invention provides a method for detecting the promoter methylation of a gene derived from a clinical sample, the method including the steps of: (a) isolating a sample DNA from a clinical sample; (b) treating the isolated sample DNA with a HpaII restriction enzyme; (c) amplifying the HpaII-treated DNA and the HpaII-untreated DNA (mock DNA) with primers capable of amplifying CpG islands; (d) hybridizing the products amplified in the step (c) with a DNA chip for detecting methylation on which either promoters containing a HpaII site in a CpG island or fragments thereof have been integrated as probes; and (e) determining that the promoters have been methylated when both the amplified product of the HpaII-treated DNA and the amplified product of the mock DNA show a positive signal.

Other aspects, features and advantages of the invention will be more fully apparent from the ensuing disclosure and appended claims.

BRIEF DESCRIPTION OF DRAWINGS

In FIG. 2, lane M is a 100 bp ladder, lane 1 is a GAPDH gene untreated with HpaII, lane 2 is a methylase-untreated GAPDH treated with HpaII, lane 3 is a methylated GAPDH gene treated with HpaII, lane 4 is a β-actin gene untreated with HpaII, and lane 5 is a β-actin gene treated with HpaII.

DETAILED DESCRIPTION OF THE INVENTION, AND PREFERRED EMBODIMENTS THEREOF

Figure 1:
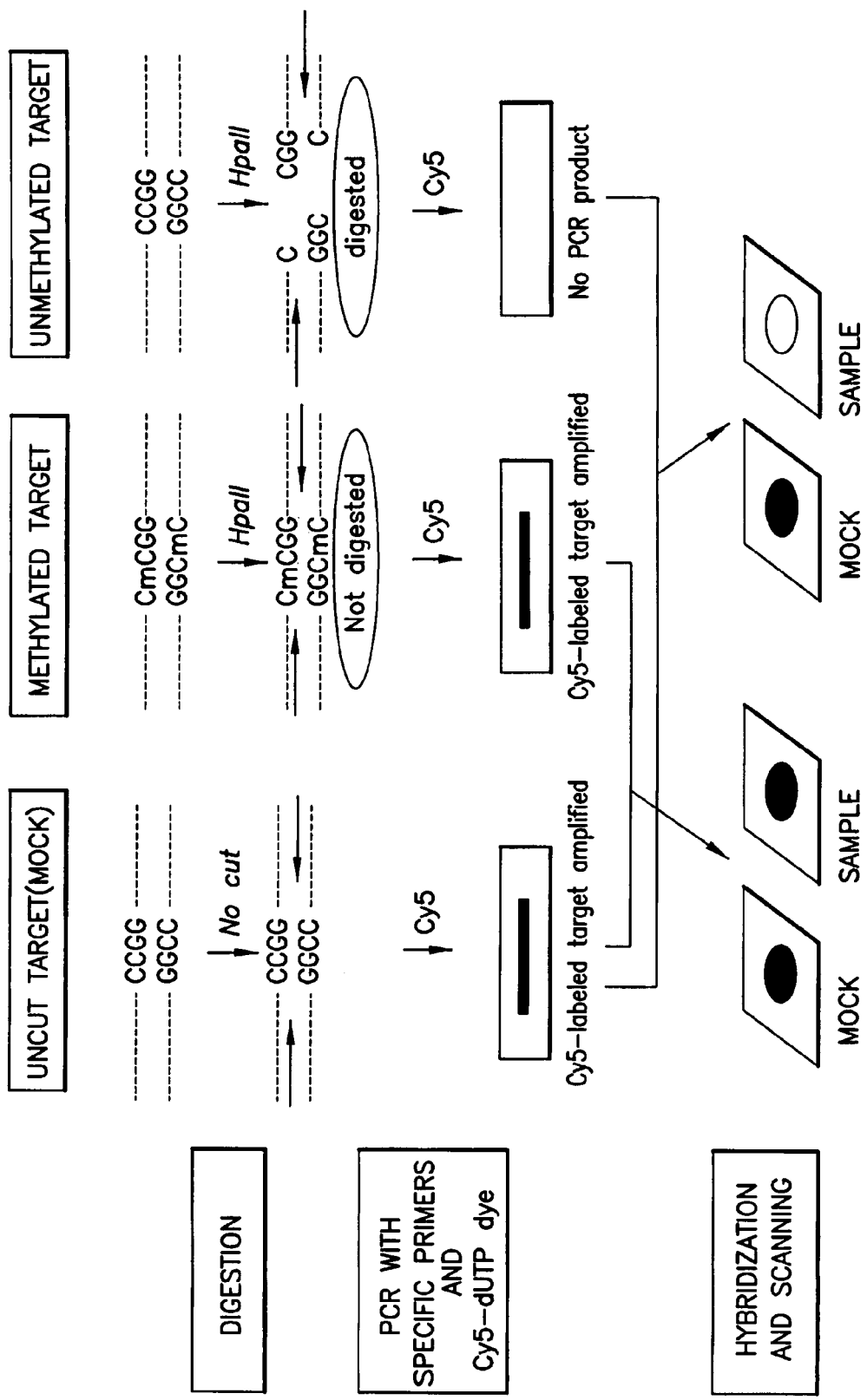
FIG. 1 is a schematic diagram showing the inventive method for detecting methylation.

The present invention relates to a method for detecting the methylation of promoters using HpaII and DNA chip. In an illustrative embodiment, such method includes the steps of: (a) isolating a sample DNA from a clinical sample; (b) treating the isolated sample DNA with a HpaII restriction enzyme; (c) amplifying the HpaII-treated DNA and the HpaII-untreated DNA (mock DNA) with primers capable of amplifying CpG islands; (d) hybridizing the products amplified in the step (c) with a DNA chip for detecting methylation on which either promoters containing a HpaII site in a CpG island or fragments thereof have been integrated as probes; and (e) determining that the promoters have been methylated when both the amplified product of the HpaII-treated DNA and the amplified product of the mock DNA show a positive signal.

In the present invention, the sample DNA preferably is a genomic DNA, and the clinical sample preferably is tissue, cells, sputum, feces, urine, cell membrane, encephalon, amniotic fluid, eyeball, intestines, or blood derived from subjects to be diagnosed or cancer-suspected patients.

In the preferred practice of the inventive method, the amplifying step is preferably PCR, and the primers capable of amplifying CpG islands are preferably primers capable of amplifying fragments containing a 5'-CCGG-3' sequence. The PCR primers used in the present invention should be designed or selected in order for at least one HpaII cutting site to be present between the internal base sequences of the DNA fragments being amplified. More preferably, the primers are any one or more primer pairs selected from the group consisting of SEQ ID NOs: 9 and 10, SEQ ID NOs: 11 and 12, SEQ ID NOs: 17 and 18, SEQ ID NOs: 19 and 20, SEQ ID NOs: 21 and 22, SEQ ID NOs: 23 and 24, SEQ ID NOs: 25 and 26, SEQ ID NOs: 27 and 28, SEQ ID NOs: 29 and 30, SEQ ID NOs: 31 and 32, SEQ ID NOs: 33 and 34, and SEQ ID NOs: 35 and 36.

In one illustrative embodiment of the present invention, the DNA chip for methylation detection is preferably integrated with 12 probes obtained by amplifying genomic DNAs derived from a clinical sample of a normal person with primer pairs of SEQ ID NOs: 9 and 10, SEQ ID NOs: 11 and 12, SEQ ID NOs: 17 and 18, SEQ ID NOs: 19 and 20, SEQ ID NOs: 21 and 22, SEQ ID NOs: 23 and 24, SEQ ID NOs: 25 and 26, SEQ ID NOs: 27 and 28, SEQ ID NOs: 29 and 30, SEQ ID NOs: 31 and 32, SEQ ID NOs: 33 and 34, and SEQ ID NOs: 35 and 36, respectively. However, probes are not limited to the above probes as long as either promoters containing an HpaII site in a CpG island or fragments thereof are used as probes. In a preferred aspect of the present invention, the 12 probes advantageously have base sequences as set forth in SEQ ID NOs: 37 to 48.

In the present invention, the term 'clinical sample' refers to sputum, feces, urine, cell membrane, encephalon, amniotic fluid, eyeball, intestines, and blood, etc. as well as a tissue and cell derived from subjects to be diagnosed, e.g., to determine whether they have cancer. The term 'mock DNA' as used herein refers to a sample DNA isolated from clinical samples with no treatment.

The HpaII enzyme, which is the restriction enzyme used in the method of the present invention, is an enzyme that recognizes and cuts a 5'-CCGG-3' base sequence present in the CpG island. However, this enzyme has a characteristic that it cannot cut the base sequence when the second cytosine of the base sequence has been methylated.

Thus, if CpG-methylated gene promoter regions are treated with HpaII, the base sequence is not cut since the enzyme cannot act on the base sequence. On the other hand, if unmethylated gene promoter regions are treated with HpaII, the CpG region is cut. When the promoter regions are subjected to PCR with a primer pair capable of amplifying the CpG island, DNA fragments of a methylated gene promoter region that have not been cut with HpaII are normally amplified by PCR, but DNA fragments of an unmethylated gene promoter region are not amplified by PCR since the promoter region is cut.

In the method of the present invention, PCR products are hybridized with a DNA chip integrated with probes of the corresponding promoter regions. Then, the methylation of the promoters is determined by the presence or absence of a positive signal. Specifically, when a positive signal is detected, it is determined that the promoters were methylated, and when the positive signal is not detected, it is determined that the promoters are not methylated (FIG. 1).

EXAMPLES

The present invention will hereinafter be described in further detail by examples. It will however be obvious to a person skilled in the art that these examples can be modified into various different forms and the present invention is not limited to or by the examples. These examples are presented to further illustrate the present invention.

In the following examples, although the methylation of promoters was measured using genomic DNAs derived from human placenta, tonsil cancer tissue, and colon cancer tissue, it is obvious to a person skilled in the art that the use of genomic DNAs derived from other biological material, such as cell membranes, blood, saliva, feces, urine, cerebral fluid, eyeballs, internal organs, kidneys, prostate gland, lungs, breast, liver, tonsils, colon, or tissue packed in a microscope slide for cell tissue, is also possible.

Furthermore, in the following examples, although Cy5-dUTP was added to a PCR reaction solution such that an amplification product was labeled with the fluorescent dye, any other markers capable of labeling DNA when added during a PCR process may also be used without limitations.

Example 1

Measurement of Methylation of GAPDH and β-Actin cDNAs According to the Invention In order to verify the cutting ability of an HpaII restriction enzyme according to methylation and the results of DNA chip hybridization according to a cut state, GAPDH and β-actin genes were used. The GAPDH gene contains one HpaII cutting site at the middle portion, and the β-actin gene contains two HpaII cutting sites. Each cDNA of the GAPDH (GenBank no. BC026907) and β-actin (GenBank no. BC002409) used in the present invention was cloned into a TOPOpCR2.1 vector (Invitrogen, USA) and then amplified by PCR with each of M13 primers (SEQ ID NO: 1 to SEQ ID NO: 4).

```
GAPDH-sense
5'-tcaacggatttggtcgtatt-3':      (SEQ ID NO: 1)

GAPDH-antisense
5'-tagaggcagggatgatgttc-3':      (SEQ ID NO: 2)

β-actin-sense
5'-cccagatcatgtttgagacc-3':      (SEQ ID NO: 3)
```

The composition of a PCR reaction solution is shown in Table 1 below. The PCR reaction consisted of reaction at 94° C. for 10 minutes, followed by 30 cycles of 1 minute at 94° C., 1 minute at 55° C. and 1 minute at 72° C., and then reaction at 72° C. for minutes.

TABLE 1

|  | GAPDH | β-actin |
| --- | --- | --- |
| Template DNA(10 ng/μl) | 1 μl | 1 μl |
| 10× buffer | 5 μl | 5 μl |
| 2.5 mM dNTP | 4 μl | 4 μl |
| Primer(10 pmol/μl) | 2 μl | 2 μl |
| Taq polymerase (10U/μl) | 0.5 μl | 0.5 μl |
| Distilled water | 37.5 μl | 37.5 μl |

5 μl of 10×HpaII methylase buffer, 2.5 μl of HpaII methylase (4 U/μl) and 0.125 μl of 400×SAM were added to 1 μg of the PCR product of the GAPDH gene, and the mixture was diluted with distilled water to a final volume of 50 μl. Then, the solution was subjected to in vitro methylation at 37° C. for 4 hours so as to artificially methylate the GAPDH gene. On the other hand, the PCR product of the β-actin gene was not methylated.

Figure 2:
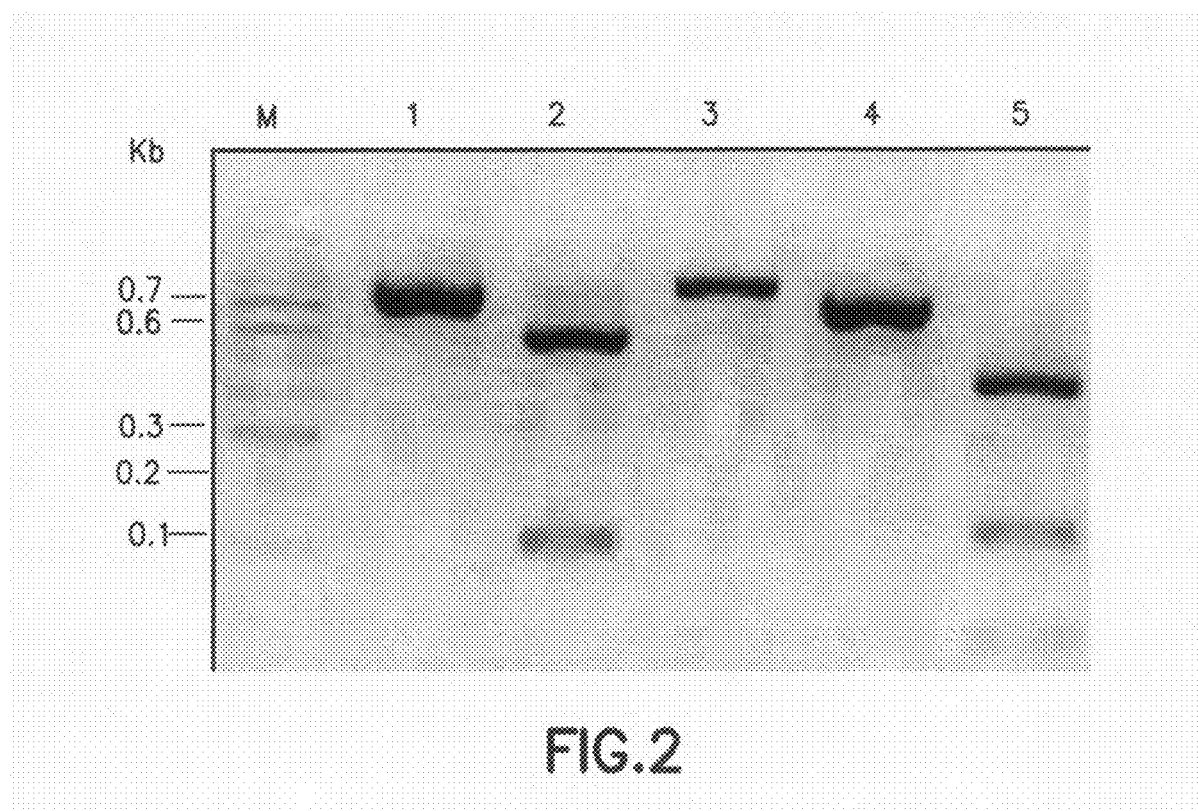
FIG. 2 shows the results of 2% agarose gel electrophoresis for a methylated GAPDH gene and an unmethylated β-actin gene, each of which have been treated with restriction enzyme HpaII, in order to examine whether the gene fragments had been cut.

The methylated GAPDH gene and the unmethylated β-actin gene were both treated with restriction enzyme HpaII, and electrophoresed on 2% agarose gel to examine whether the gene fragments were cut or not (FIG. 2). In FIG. 2, lane 1 represents the GAPDH gene untreated with HpaII, and lane 2 represents the methylase-untreated GAPDH gene treated with HpaII and showed fragments cut with HpaII. Lane 3 is the methylated GAPDH gene treated with HpaII, and did not show cut fragments. Lane 4 is the β-actin gene untreated with HpaII, and lane 5 is the β-actin gene treated with HpaII. In lane 5, three fragments where two HpaII cutting sites on the β-actin gene have been cut could be observed. Such results suggest that the methylated GAPDH gene is not cut with HpaII, and the unmethylated β-actin gene is cut with HpaII.

In order for the methylated GAPDH gene sample treated with HpaII and the unmethylated β-actin gene sample treated with HpaII to be hybridized with DNA chips, each nested PCR was performed with each of primers (SEQ ID NOs: 5 to 8). The obtained PCR product was fluorescence-labeled by adding Cy5-dUTP to each PCR reaction solution. The composition of each of the reaction solutions is shown in Table 2 below. In each PCR reaction, the reaction solution was subjected to reaction at 94° C. for 10 minutes, followed by 30 cycles of 1 minute at 94° C., 1 minute at 55° C. and 1 minute at 72° C., and then reaction at 72° C. for 5 minutes.

```
GAPDH nested sense
5'-gggtgtgaaccatgagaagta tg-3':   (SEQ ID NO: 5)

GAPDH nested antisense
5'-ggcagggatgatgttctg gag-3':     (SEQ ID NO: 6)

β-actin nested sense
5'-ggctgtgctatccctgta cgc-3':     (SEQ ID NO: 7)

β-actin nested antisense
5'-ccagggcgacgtagcaca gc-3':      (SEQ ID NO: 8)
```

TABLE 2

Composition of nested PCR solution for Cy5-dUTP labeling

|  | GAPDH-IVM | β-actin |
|---|---|---|
| HpaII treated DNA | 200 pg | 200 pg |
| 10× Taq buffer | 2.5 μl | 2.5 μl |
| 2.5 mM dNTP mix | 2 μl | 2 μl |
| Cy5-dUTP(1 mM) | 0.5 μl | 0.5 μl |
| Primer | 2 μl | 2 μl |
| Taq polymerase | 0.5 μl | 0.5 μl |
| Distilled water | final volume to 25 μl | |

The resulting PCR amplification product was purified, eluted in 100 μl of distilled water, and then hybridized with DNA chips integrated with the cDNA probes of the GAPDH and β-actin gene. The composition of each reaction solution for hybridization is shown in Table 3 below.

TABLE 3

|  | GAPDH-IVM | β-actin |
|---|---|---|
| Eluted DNA | 20 μl | 20 μl |
| 20× SSC | 17.5 μl | 17.5 μl |
| 10% SDS | 3 μl | 3 μl |
| Salmon sperm DNA (5 mg/ml) | 1 μl | 1 μl |
| Distilled water | final volume to 100 μl | |

The DNA chip integrated with the cDNA probes of GAPDH was fabricated in the following manner. Total RNA was isolated from human placenta, and 5 μg of the total RNA was mixed with 200 ng of a primer of SEQ ID NO: 2 at a volume of 15.4 μl, treated for 10 minutes at 65° C., and then subjected to reverse transcription reaction, thus synthesizing cDNAs. The reverse transcription reaction was performed with SuperscriptII (Invitrogen) at a total volume of 30 μl. 6 μl of 5× first strand buffer, 3.0 μl of 0.1M DTT, 1.0 μl of dNTPs (each 10 mM) and 1.0 μl of SuperscriptII (Invitrogen, 200 units) were added to the reaction solution to be a final volume of 30 μl. The mixture was left as it is at 42° C. for 2 hours so as to synthesize single stranded cDNA. 1/10 of the reverse transcription mixture was taken to use in PCR reaction for amplifying the GAPDH cDNA. The composition of the PCR solution consisted of 3 μl of single stranded cDNA, 2.51 μl of 10× buffer, 2 μl of 2.5 mM dNTP, 1 μl of Taq polymerase (5 units, Solgent), and each 1 μl of primers of SEQ ID NOs: 1 and 2 (10 pmol/μl). The composition was diluted in distilled water to a final volume of 25 μl, and then subjected to PCR under the following conditions: 10 minutes at 94° C., followed by 30 cycles of 1 minute at 94° C., 1 minute at 55° C., and 1 minute at 72° C., and then 10 minutes at 72° C. The resulting PCR product was cloned into a TOPOpCR2.1 plasmid vector (Invitrogen), after which the GAPDH cDNA was PCR-amplified again with primers of SEQ ID NOs: 5 and 6. This PCR reaction was performed under the same conditions as described above.

The DNA chip spotted with the cDNA probes of the β-actin gene was fabricated in the following manner. The β-actin gene was subjected to reverse transcription with a primer of SEQ ID NO: 4 under the same conditions as the case of the GAPDH gene, followed by PCR with primers of SEQ ID NO: 3 and 4. These PCR products were cloned into a TOPOpCR2.1 plasmid vector (Invitrogen). The β-actin cDNA was amplified using primers of SEQ ID NOs: 7 and 8 in the same manner as in the case of the GAPDH gene.

The resulting amplification products were suspended in 50% DMSO solution to 200-250 ng/μl, integrated on a Corning UltraGAPS glass slide (Corning), left as they were at room temperature for 16 hours, and then cross-linked by irradiation with 350 mJ ultraviolet rays.

After hybridization, each of the reaction solutions was boiled at 100° C. for 3 minutes, and applied on the DNA chips spotted with the probes of each of GAPDH and β-actin genes. Then, the resulting chips were allowed to react at 65° C. for 2 hours, thus completing hybridization. After the reaction, the DNA chips were washed, and scanned with Axon scanner 400B (Axon Instrument, CA, USA) (FIG. 3).

Figure 3:
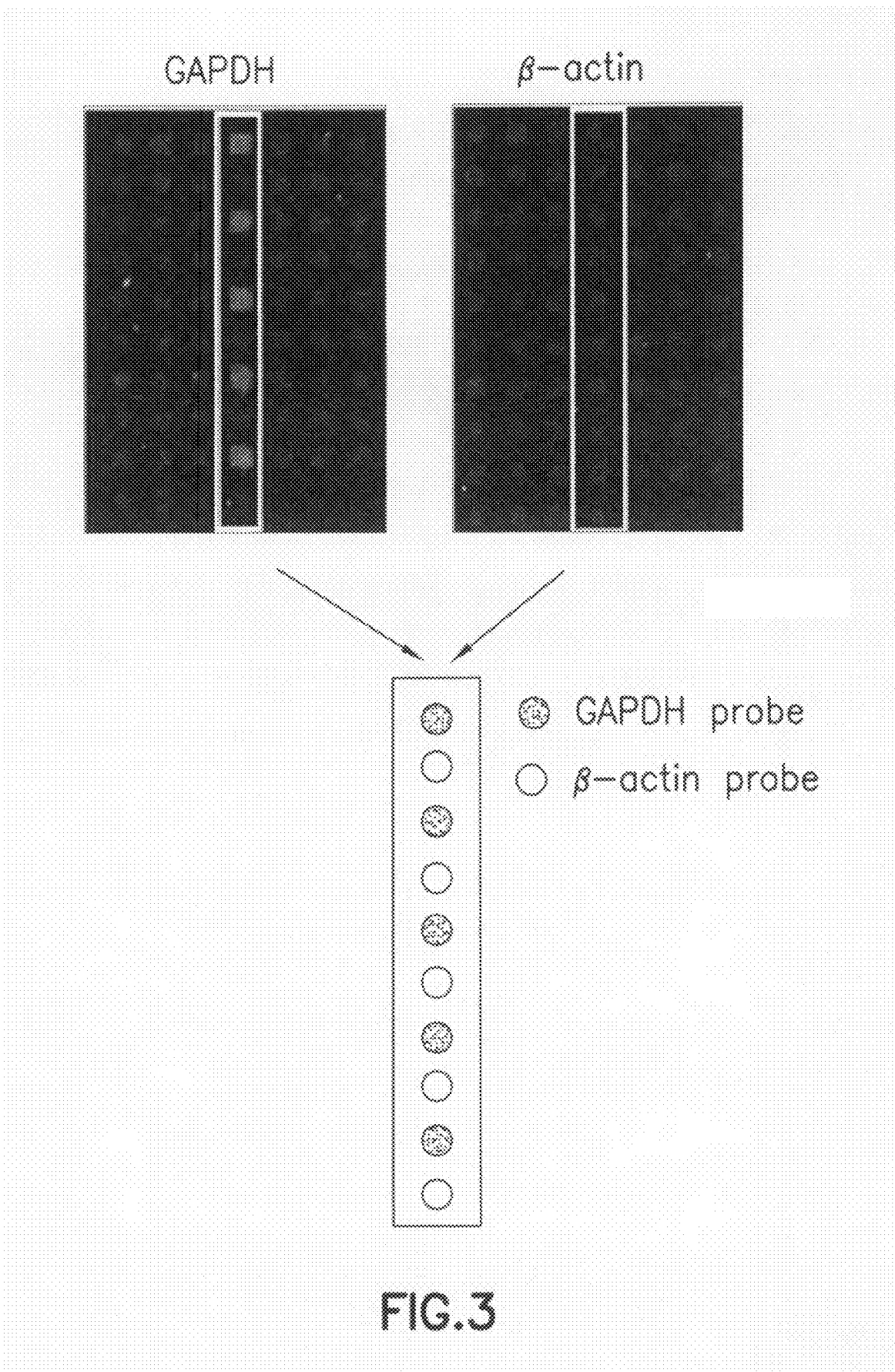
FIG. 3 shows scanning photographs of DNA chips with which PCR products of a methylated GAPDH gene and an unmethylated β-actin gene have been hybridized.

The scanning results showed that, in the methylated GAPDH, a hybridization signal was observed since the methylated GAPDH was not cut even by HpaII treatment so as to produce normal PCR products (left panel of FIG. 3), but in the unmethylated β-actin, a hybridization signal was not observed since the unmethylated β-actin was cut by HpaII treatment so that PCR products were not produced (right panel of FIG. 3). This shows that the inventive method allows the methylation of genes to be effectively detected.

Example 2

Detection of Methylation of Cancer Cell Lines

In this Example, the methylation of promoters was detected on human cancer cell lines. As promoters to be measured for methylation, promoters of an MAGEB2 gene (promoter of melanoma associated antigen 2, GenBank No. U93163) and an RAR-β gene (retinoic acid receptor-β, GenBank No. NM-000965), which are known to have been methylated in colon cancer tissue, were used (De Smet, C. et al., *Mol. Cell. Bio.*, 19:7327, 1999; Virmani, A. K. et al., *J. Natl. Cancer Institut.*, 92:1303, 2000).

In this Example, the genomic DNA of a Caco-2 cell line (ATCC HTB37) was used to measure the methylation of the genes. First, the genomic DNA of a Caco-2 cell line was isolated and treated with HpaII, which is a restriction enzyme for cutting a CpG site. In the restriction enzyme treatment, a reaction solution having the following composition was used: 2 μl of Caco-2 cell line genomic DNA, 5 μl of 10×HpaII buffer, 2 μl of HpaII (10 U/μl), and distilled water to a final volume of 50 μl.

The Caco-2 cell line genomic DNAs treated with HpaII were purified, and subjected to PCR amplification with each of primers (SEQ ID NOs: 9 to 12) in order to amplify MAGEB2 gene promoter and RAR-β gene promoter regions. The amplification reactions were performed with the addition of Cy5-dUTP in the same manner as in Example 1.

```
MAGEB2 sense
5'-gcagagagagagtcttggctttc-3':       (SEQ ID NO: 9)

MAGEB2 antisense
5'-cttgactgccgaccagtcctg-3':         (SEQ ID NO: 10)

RAR-β sense
5'-gtgacagaagtagtaggaagtga-3':       (SEQ ID NO: 11)

RAR-β antisense
5'-gatctcccttgcactgaatgtc-3':        (SEQ ID NO: 12)
```

Each of the amplified PCR products was hybridized with a DNA chip spotted with each of MAGEB2 and RAR-β probes, in the same manner as in Example 1. The DNA chips used in the present invention, which have been integrated with MAGEB2 and RAR-β probes respectively, were fabricated in the following manner. In order to fabricate the probes of MAGEB2 and RAR-β methylation promoter portions, human placenta genomic DNAs were isolated and used to amplify MAGEB2 promoter probes with primers of SEQ ID NOs: 9 and 10 and to amplify RAR-β promoter probes with primers of SEQ ID NOs: 11 and 12. Then, DNA chips were fabricated in the same manner as described in Example 1.

Figure 4:
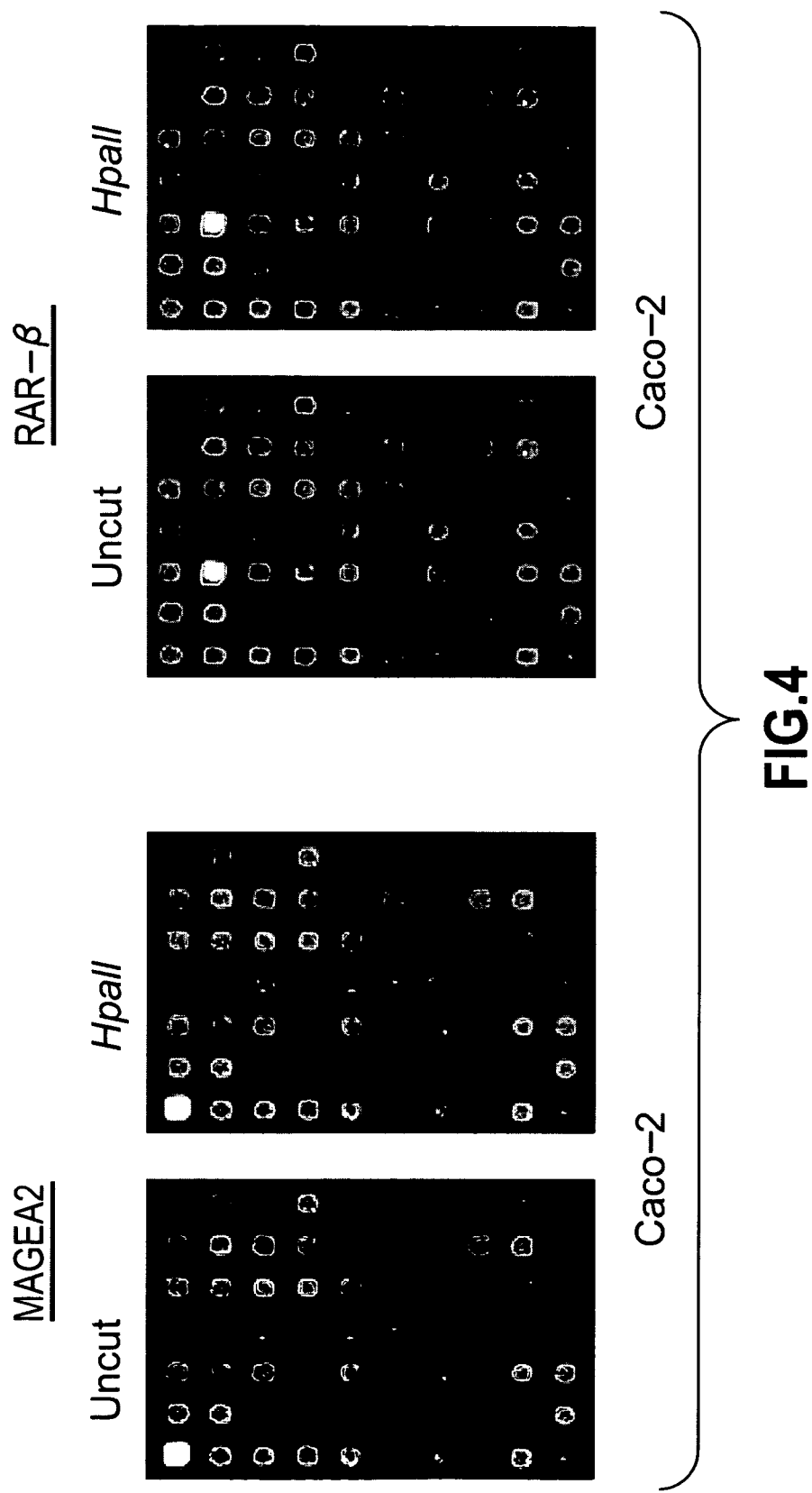
FIG. 4 shows scanning photographs of DNA chips illustrating the measurement of methylation of a melanoma antigen family B2 (MAGEB2) gene promoter and a Retinoic acid receptor beta (RAR-β) gene promoter by the inventive method.

From the hybridization results as shown in FIG. 4, it could be found that, when the genomic DNAs of the Caco-2 cell line, which is a colon cell line was treated with HpaII, a positive signal was observed in both the HpaII-treated and HpaII-untreated samples for the MAGEB2 gene promoter and RAR-β gene promoter probes, thereby indicating that both the MAGEB2 gene promoter and the RAR-β gene promoter were methylated.

In order to prove by other method that the two promoter sites amplified by the PCR have been methylated, bisulfite sequencing was performed. If DNA is treated with bisulfite, unmethylated cytosine changes into uracil whereas methylated cytosine does not change. 1 μg of the Caco-2 genomic DNA isolated as described above was subjected to bisulfite modification (Sato, N. et al., Cancer Research, 63:3735, 2003) with an MSP bisulfite modification kit (In2Gen, Inc., Korea). The bisulfite-treated Caco-2 genomic DNAs were amplified by PCR with each of primers (SEQ ID NOs: 13 to 16), and cloned into a Topo vector (Invitrogen, USA) to analyze a base sequence.

```
MAGE BF sense
5'-gggggtattgtttggaggttgg-3'         (SEQ ID NO: 13)

MAGE BF antisense
5'-aaaaattcacccctaactaac caaac-3'    (SEQ ID NO: 14)

RAR-β BF sense
5'-ggtaggagggtttatttttgtta-3'        (SEQ ID NO: 15)

RAR-β BF antisense
5'-cccaaaaaaatcccaaattct cc-3'       (SEQ ID NO: 16)
```

Figure 5:
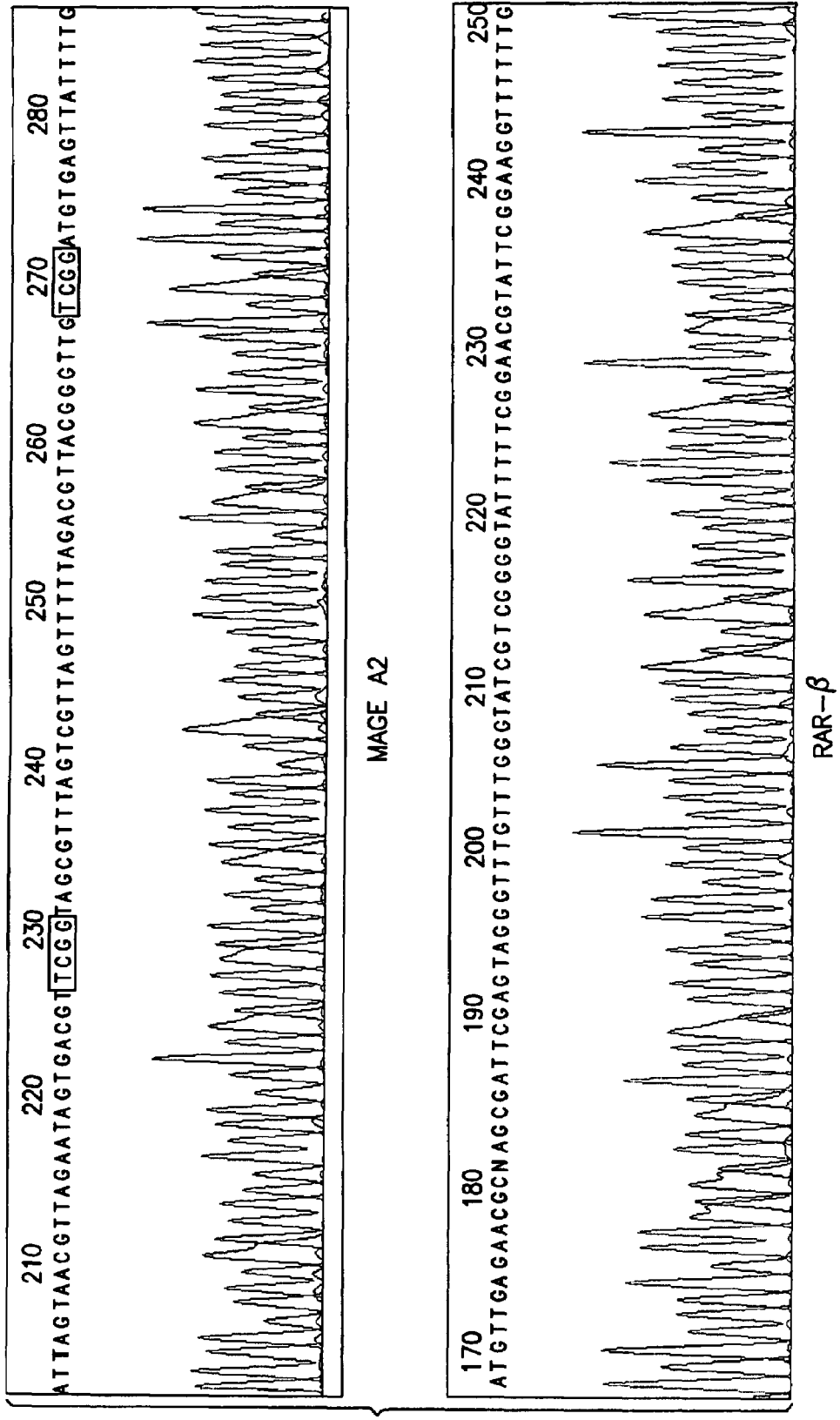
FIG. 5 shows the results of bisulfite sequencing conducted to determine the methylation of a MAGEB2 gene promoter and a RAR-β gene promoter.

The results of base sequence analysis of each sample showed that cytosine was detected in all CpG island-containing regions in the base sequences of the MAGEB2 gene promoter and the RAR-β gene promoter, thereby indicating that the two gene promoters were all methylated (FIG. 5).

Example 3

Detection of Methylation Using Clinical Sample

In order to examine if the inventive method for detecting methylation is applicable to clinical samples, methylation was detected using the cancer tissue genomic DNA of actual cancer patients. In this Example, methylation was measured on 12 genes (Table 4) in which the CpG island of their promoters is known to be methylated in human cancer tissue. In Table 4, the following abbreviations are used: MAGEB2 is melanoma antigen family B2 promoter, APC is adenomatosis polyposis coli promoter, CDH13 is cadherin 13 promoter, MTHFR is 5,10-methylenetetrahydrofolate reductase promoter, CALCA is calcitonin/calcitonin-related polypeptide, alpha promoter, AR is androgen receptor promoter, S100A2 is S100 calcium binding protein A2 promoter, SRBC is Serpentine Receptor, class BC promoter, RAR-β is Retinoic acid receptor beta promoter, EDN1 is endothelin 1 promoter, CFTR is cystic fibrosis transmembrane conductance regulator promoter and BLT1 is leukotriene $B_4$ ($LTB_4$) receptor 1 promoter.

TABLE 4

| Name of genes | GenBank accession no. |
|---|---|
| MAGEB2 | U93163 |
| APC | U02909 |
| CDH13 | AB001090 |
| MTHFR | AF105977 |
| CALCA | X15943 |
| AR | M58158 |
| S100A2 | Y07755 |
| SRBC | AF08198 |
| RAR-beta | X56849 |
| EDN1 | J05008 |
| CFTR | M58478 |
| BLT1 | AB008193 |

Genomic DNAs from human normal placenta tissue, tonsil cancer tissue and colon cancer tissue were isolated, and sites containing at least one HpaII cutting site in a CpG island of the promoter sites of the genes were amplified by PCR with primers shown in Table 5 below. Furthermore, the genomic DNAs of human normal placenta tissue were amplified with primers shown in Table 5 so as to obtain 12 probes (SEQ ID NO: 37 to SEQ ID NO: 48). Then, the probes were integrated on a glass slide (Corning UltraGAPS, Corning) so as to fabricate a DNA chip.

Each of the restriction enzyme HpaII-untreated genomic DNA groups and HpaII-treated genomic DNA groups of placenta tissue, tonsil cancer tissue and colon cancer tissue was added with each pair of PCR primers shown in Table 5, and simultaneously amplified in the presence of Cy5-dUTP. The composition of a PCR reaction solution for each sample is shown in Table 6 below.

TABLE 5

| Name of genes | Sense primer<br>Antisense primer | Size of PCR product (bp) |
|---|---|---|
| MAGEB2 | (SEQ ID NO: 9): 5'-gca gag aga gag tct tgg ctt tc-3'<br>(SEQ ID NO: 10): 5'-ctt gac tgc cga cca gtc ctg-3' | 501 |
| APC | (SEQ ID NO: 17): 5'-cag gca acc cag acg tcc aga g-3'<br>(SEQ ID NO: 18): 5'-cag tgc cac cct ggc ggg ct-3' | 576 |
| CDH13 | (SEQ ID NO: 19): 5'-ccg tgc aat tcc att ctc tgg a-3'<br>(SEQ ID NO: 20): 5'-cgc aca gaa cga gcg gag ttc-3' | 409 |

TABLE 5-continued

| Name of genes | Sense primer Antisense primer | Size of PCR product (bp) |
|---|---|---|
| MTHFR | (SEQ ID NO: 21): 5'-gct gcc tgc ccc ctg atg c-3'<br>(SEQ ID NO: 22): 5'-ccc cag gca cca cca ctc c-3' | 346 |
| CALCA | (SEQ ID NO: 23): 5'-gga tca gag ttg gaa gag tcc c-3'<br>(SEQ ID NO: 24): 5'-cct ccc ago gcc agc gac t-3' | 382 |
| AR | (SEQ ID NO: 25): 5'-gga ccc gac tcg caa act gt-3'<br>(SEQ ID NO: 26): 5'-gct ggc gtg gtg cgt ccc t-3' | 195 |
| S100A2 | (SEQ ID NO: 27): 5'-cca cag ttc tct cat tcc agc-3'<br>(SEQ ID NO: 28): 5'-ctc agg att ctt ttt gca gca ac-3' | 578 |
| SRBC | (SEQ ID NO: 29): 5'-gct acc caa gag gac gaa ata aa-3'<br>(SEQ ID NO: 30): 5'-ctg gct gca cta cgg tca gg-3' | 629 |
| RAR-β | (SEQ ID NO: 11): 5'-gtg aca gaa gta gta gga agt ga-3'<br>(SEQ ID NO: 12): 5'-gat ctc cct tgc act gaa tgt c-3' | |
| EDN1 | (SEQ ID NO: 31): 5'-ggt aca cag gcc ata tag gaa c-3'<br>(SEQ ID NO: 32): 5'-ccg aat ccc tgg gca tca gg-3' | 620 |
| CFTR | (SEQ ID NO: 33): 5'-cct cca gcg ttg cca act gg-3'<br>(SEQ ID NO: 34): 5'-cgt ctg ggc tca agc tcc ta-3' | 443 |
| BLT1 | (SEQ ID NO: 35): 5'-gtg agc gcc atc gtg ctt gc-3'<br>(SEQ ID NO: 36): 5'-cac cac ttt cag ctg agg gg-3' | 332 |

TABLE 6

| | Placenta | Placenta/HpaII | Tonsil | Tonsil/HpaII | Colon | Colon/HpaII |
|---|---|---|---|---|---|---|
| Genomic DNA | 200 ng | 200 ng | 200 ng | 200 ng | 200 ng | 200 ng |
| 10× buffer | 2.5 μl | 2.5 μl | 2.5 μl | 2.5 μl | 2.5 μl | 2.5 μl |
| 2.5 mM dNTP | 2 μl | 2 μl | 2 μl | 2 μl | 2 μl | 2 μl |
| Cy5-dUTP | 0.5 μl | 0.5 μl | 0.5 μl | 0.5 μl | 0.5 μl | 0.5 μl |
| 12 pair primer (each 10 pmol) | 12 μl | 12 μl | 12 μl | 12 μl | 12 μl | 12 μl |
| Taq polymerase (5 units) | 1 μl | 1 μl | 1 μl | 1 μl | 1 μl | 1 μl |
| Distilled water | | | Final volume to 25 μl | | | |

Figure 6:
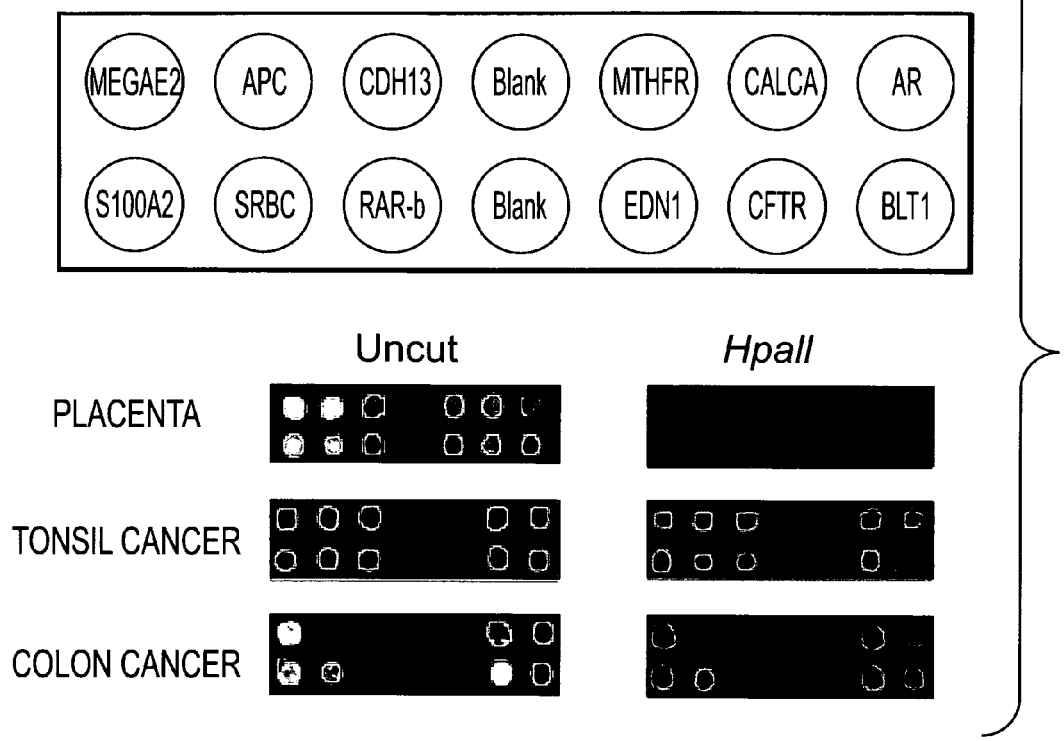
FIG. 6 shows scanning photographs of DNA chips which illustrate the measurement of methylation of gene promoters derived from human placenta, tonsil cancer tissue, and colon cancer tissue, by the inventive method.

The amplified products were hybridized with a DNA chip spotted with 12 probes, and then scanned to determine whether the products have been methylated or not. From the scanning results as shown in FIG. 6, it was found that, for the genomic DNAs of normal placenta tissue, a positive signal was observed only in the HpaII-untreated group, and not observed in the HpaII-treated group, thereby indicating that methylation did not occur in the CpG islands of all the 12 gene promoters. On the other hand, for the genomic DNAs of tonsil cancer tissue and colon cancer tissue, a positive signal was observed in both the HpaII-untreated group and the HpaII-treated group, thereby indicating that the CpG islands of the corresponding gene promoters were methylated. Also, it was shown that, for the genomic DNAs of tonsil cancer tissue, the CpG islands of MAGEB2, APC, CDH13, CALCA, AR, S100A2, SRBC, RAR-β and CFTR gene promoters were methylated, and for the genomic DNAs of colon cancer tissue, the CpG islands of MAGEB2, CALCA, AR, S100A2, SRBC, CFTR and BLT1 gene promoters were methylated.

Such results evidence the utility of the inventive method for detecting methylation, as enabling the methylation of cancer-associated gene promoters to be detected in a rapid, accurate and simple manner.

As described above in detail, the present invention provides a method for detecting the methylation of promoters in a rapid and accurate manner at low cost, by the approach of cutting DNAs derived from clinical samples or subjects to be diagnosed, with restriction enzyme HpaII, amplifying the cut DNAs by PCR with primers capable of amplifying CpG islands, and determining the presence or absence of the PCR amplification products using a DNA chip for methylation detection.

Unlike the prior methods, such inventive method allows the methylation of gene promoters to be detected in a simple and economical manner, and thus is useful for the diagnosis of diseases such as cancer, in which the methylation of gene promoters occurs.

While the present invention has been described with reference to particular illustrative features and embodiments, it is not intended to be restricted thereby in relation to the appended claims. It will be appreciated that those skilled in the art can change or modify the specific features and embodiments without departing from the scope and spirit of the present invention.

What is claimed is:

1. A method for detecting the promoter methylation of one or more genes in a genomic DNA sample isolated from a human clinical sample, wherein the one or more genes are selected from the group consisting of human melanoma antigen family B2 (MAGEB2) gene, human adenomatosis polyposis coli (APC) gene, human cadherin 13 (CDH13) gene, human 5,10-methylenetetrahydrofolate reductase (MTHFR) gene, the gene of human calcitonin/calcitonin-related polypeptide, Alpha (CALCA), human androgen receptor (AR) gene, human S100 calcium binding protein A2 (S100A2) gene, the gene of human Serpentine Receptor, class BC (SRBC), human Retinoic acid receptor beta (RAR-β) gene, human endothelin 1 (EDN1) gene, human cystic fibrosis transmembrane conductance regulator (CFTR) gene and human leukotriene B4 receptor 1 (BLT1) gene, the method comprising the steps of:
   (a) isolating a genomic DNA sample containing different gene promoters or fragments thereof from the clinical sample;
   (b) treating a quantity of the isolated genomic DNA sample of step (a) with a HpaII restriction enzyme and producing HpaII-treated genomic DNA, wherein another quantity of the isolated genomic DNA sample of step (a) is untreated with the HpaII restriction enzyme and is HpaII-untreated genomic DNA;
   (c) independently amplifying the HpaII-treated genomic DNA and the HpaII-untreated genomic DNA with primers capable of amplifying CpG islands, wherein the primers are one or more primer pairs selected from the group consisting of SEQ ID NOs: 9 and 10, SEQ ID NOs: 11 and 12, SEQ ID NOs: 17 and 18, SEQ ID NOs: 19 and 20, SEQ ID NOs: 21 and 22, SEQ ID NOs: 23 and 24, SEQ ID NOs: 25 and 26, SEQ ID NOs: 27 and 28, SEQ ID NOs: 29 and 30, SEQ ID NOs: 31 and 32, SEQ ID NOs: 33 and 34, and SEQ ID NOs: 35 and 36 and producing amplified products of the HpaII-treated genomic DNA and amplified products of the HpaII-untreated genomic DNA;
   (d) hybridizing the amplified products of the HpaII-treated genomic DNA in step (c) with one or more nucleic acid probes on a DNA chip wherein each of the one or more probes is a human gene promoter region or a fragment thereof containing a HpaII site in one of its CpG islands and hybridizing the amplified products of the HpaII-untreated genomic DNA in step (c) with the one or more nucleic acid probes on said DNA chip, and producing a DNA chip reacted with the amplified product of the HpaII-treated genomic DNA and a DNA chip reacted with the amplified product of the HpaII-untreated genomic DNA, and,
   wherein the promoter region is a promoter selected from the group consisting of human melanoma antigen family B2 (MAGEB2) promoter, human adenomatosis polyposis coli (APC) promoter, human cadherin 13 (CDH13) promoter, human 5,10-methylenetetrahydrofolate reductase (MTHFR) promoter, the promoter of human calcitonin/calcitonin-related polypeptide, alpha (CALCA), human androgen receptor (AR) promoter, human S 100 calcium binding protein A2 (S 100A2) promoter, the promoter of human Serpentine Receptor, class BC (SRBC), human Retinoic acid receptor beta (RAR-β) promoter, human endothelin 1 (EDN1) promoter, human cystic fibrosis transmembrane conductance regulator (CFTR) promoter and human leukotriene B4 receptor 1 (BLT1) promoter; and
   (e) comparing hybridization results of the DNA chip reacted with the amplified product of the HpaII-treated genomic DNA with hybridization results of the DNA chip reacted with the amplified product of the HpaII-untreated genomic DNA and detecting the promoter methylation of the one or more genes in the genomic DNA sample isolated from the human clinical sample, wherein the promoters of the one or more genes in the isolated genomic DNA sample from the clinical sample are methylated when both the DNA chip reacted with the amplified product of the HpaII-treated genomic DNA and the DNA chip reacted with the amplified product of the HpaII-untreated genomic DNA display positive hybridization signals and identical hybridization patterns.

2. The method according to claim 1, wherein the clinical sample comprises biological material selected from the group consisting of tissue, cells, sputum, feces, urine, cell membrane, encephalon, amniotic fluid, eyeball, intestines, or blood derived from subjects to be diagnosed or cancer-suspected patients.

3. The method according to claim 1, wherein said amplifying step (c) includes polymerase chain reaction (PCR).

4. The method according to claim 1, wherein the primers capable of amplifying CpG islands are capable of amplifying fragments containing a 5'-CCGG-3' sequence.

5. The method according to claim 1, wherein the one or more nucleic acid probes on the DNA chip are 12 probes obtained by amplifying genomic DNAs derived from a clinical sample of a normal human with primer pairs of SEQ ID NOs: 9 and 10, SEQ ID NOs: 11 and 12, SEQ ID NOs: 17 and 18, SEQ ID NOs: 19 and 20, SEQ ID NOs: 21 and 22, SEQ ID NOs: 23 and 24, SEQ ID NOs: 25 and 26, SEQ ID NOs: 27 and 28, SEQ ID NOs: 29 and 30, SEQ ID NOs: 31 and 32, SEQ ID NOs: 33 and 34, and SEQ ID NOs: 35 and 36, respectively.

6. The method according to claim 5, wherein the 12 probes have nucleotide sequences consisting of SEQ ID NOs: 37 to 48.

* * * * *